United States Patent
Szelenyi et al.

(10) Patent No.: US 8,557,851 B2
(45) Date of Patent: Oct. 15, 2013

(54) COMBINATIONS OF FLUPIRTINE AND SODIUM CHANNEL INHIBITING SUBSTANCES FOR TREATING PAINS

(75) Inventors: Istvan Szelenyi, Schwaig (DE); Kay Brune, Marloffstein (DE); Robert Hermann, Hanau (DE); Mathia Locher, Ronneburg (DE)

(73) Assignee: MEDA Pharma GmbH & Co. KG, Bad Homburg (DE)

( * ) Notice: Subject to any disclaimer, the term of this patent is extended or adjusted under 35 U.S.C. 154(b) by 236 days.

(21) Appl. No.: 12/403,213

(22) Filed: Mar. 12, 2009

(65) Prior Publication Data

US 2009/0176814 A1    Jul. 9, 2009

Related U.S. Application Data

(63) Continuation of application No. 10/727,658, filed on Dec. 5, 2003, now abandoned.

(30) Foreign Application Priority Data

Oct. 20, 2003 (DE) .................................. 103 49 729

(51) Int. Cl.
*A61K 31/44* (2006.01)
*A61K 31/4453* (2006.01)

(52) U.S. Cl.
USPC ........................... 514/352; 514/317; 514/906

(58) Field of Classification Search
None
See application file for complete search history.

(56) References Cited

U.S. PATENT DOCUMENTS

| | | | |
|---|---|---|---|
| 4,442,084 A | 4/1984 | Römer | |
| 4,668,684 A | 5/1987 | Tibes et al. | |
| 4,778,799 A | 10/1988 | Tibes et al. | |
| 5,162,346 A | 11/1992 | Lobisch et al. | |
| 5,284,861 A | 2/1994 | Lobisch et al. | |
| 5,384,330 A | 1/1995 | Dieter et al. | |
| 5,760,007 A | 6/1998 | Shank et al. | |
| 5,849,789 A | 12/1998 | Rostock et al. | |
| 5,852,053 A | 12/1998 | Rostock et al. | |
| 5,925,634 A | 7/1999 | Olney | |
| 6,117,900 A | 9/2000 | Rundfeldt et al. | |
| 6,211,171 B1 | 4/2001 | Sawynok et al. | |
| 6,281,211 B1 | 8/2001 | Cai et al. | |
| 6,348,486 B1 | 2/2002 | Argentieri et al. | |
| 6,451,857 B1 | 9/2002 | Hurtt et al. | |
| 6,472,165 B1 | 10/2002 | Rundfeldt et al. | |
| 6,500,455 B1 | 12/2002 | Frantsits | |
| 6,537,991 B1 | 3/2003 | Shaw et al. | |
| RE38,115 E | 5/2003 | Smith et al. | |
| 7,419,981 B2 | 9/2008 | Field et al. | |

FOREIGN PATENT DOCUMENTS

| | | |
|---|---|---|
| CA | 2542434 | 5/2005 |
| DE | 3604575 A1 | 8/1986 |
| DE | 103 49 729.3 | 10/2003 |
| DE | 103 49 729 .3 | 10/2003 |
| DE | 103 59 335 | 5/2005 |
| EP | 189788 A1 | 8/1986 |
| EP | 1813285 A1 | 8/2007 |
| JP | 2000-143510 A | 5/2000 |
| RU | 2006117525 | 12/2005 |
| WO | WO 00/59487 A2 | 10/2000 |
| WO | WO 00/59508 A1 | 10/2000 |
| WO | WO 01/01970 A2 | 1/2001 |
| WO | WO 01/22953 A2 | 4/2001 |
| WO | WO 2005/039576 | 5/2005 |

OTHER PUBLICATIONS

Pratzel et al., Pain, 1996, vol. 67, pp. 417-425.*
Balano KB. Anti-inflammatory drugs and myorelaxants. Pharmacology and clinical use in musculoskeletal disease. Prim Care. Jun. 1996;23(2):329-34.
Richards BL, Whittle SL, Buchbinder R. Muscle relaxants for pain management in rheumatoid arthritis. Cochrane Database Syst Rev. Jan. 18, 2012;1:CD008922. pp 1-11.
Argoff CE. Pharmacologic management of chronic pain. J Am Osteopath Assoc. Sep. 2002;102(9 Suppl 3):S21-7.
Kvien TK, Viktil K. Pharmacotherapy for regional musculoskeletal pain. Best Pract Res Clin Rheumatol. Feb. 2003;17(1):137-50.
Quasthoff S, Möckel C, Zieglgänsberger W, Schreibmayer W. Tolperisone: a typical representative of a class of centrally acting muscle relaxants with less sedative side effects. CNS Neurosci Ther. 2008 Summer;14(2):107-19.
Smith HS, Barton AE. Tizanidine in the management of spasticity and musculoskeletal complaints in the palliative care population. Am J Hosp Palliat Care. Jan.-Feb. 2000;17(1):50-8).
Solaro C, Messmer Uccelli M. Pharmacological management of pain in patients with multiple sclerosis. Drugs. Jul. 9, 2010;70(10):1245-54.
Fuh JL, Chang DB, Wang SJ, Ju TH, Liu HC. Painful tonic spasms: an interesting phenomenon in cerebral ischemia. Acta Neurol Scand. Dec. 1991;84(6):534-6.
Zakrzewska JM, Linskey ME. Trigeminal neuralgia. Clin Evid (Online). Mar. 12, 2009;2009. pii: 1207.
Krafft RM. Trigeminal neuralgia. Am Fam Physician. May 1, 2008;77(9):1291-6.
Stanko JR. Review of oral skeletal muscle relaxants for the craniomandibular disorder (CMD) practitioner. Cranio. Jul. 1990;8(3):234-43.
Hersh EV, Balasubramaniam R, Pinto A. Pharmacologic management of temporomandibular disorders. Oral Maxillofac Surg Clin North Am. May 2008;20(2):197-210, vi.
Gore M, Tai KS, Sadosky A, Leslie D, Stacey BR. Use and Costs of Prescription Medications and Alternative Treatments in Patients with Osteoarthritis and Chronic Low Back Pain in Community-Based Settings. Pain Pract. Feb. 5, 2012. doi: 10.1111/j.1533-2500.2012. 00532.x. [Epub ahead of print].
Rollings HE. Carisoprodol in osteoarthritis. Clin Med (Northfield II). Aug. 1964;71:1378-80.

(Continued)

*Primary Examiner* — Savitha Rao
*Assistant Examiner* — Gregg Polansky
(74) *Attorney, Agent, or Firm* — Crowell & Moring LLP

(57) ABSTRACT

The invention relates to pharmaceutical combinations of potassium channel openers and sodium channel inhibitors, for treating pains which are accompanied by an increase in muscle tone.

9 Claims, No Drawings

(56) References Cited

OTHER PUBLICATIONS

Tarpley EL. Evaluation of diazepam (Valium) in the symptomatic treatment of rheumatic disorders. A controlled comparative study. J Chronic Dis. Jan. 1965;18:99-106.
Bhatia R, Dureja GP, Tripathi M, Bhattacharjee M, Bijlani RL, Mathur R. Role of temporalis muscle over activity in chronic tension type headache: effect of yoga based management. Indian J Physiol Pharmacol. Oct.-Dec. 2007;51(4):333-44.
Freitag FG. Preventative treatment for migraine and tension-type headaches : do drugs having effects on muscle spasm and tone have a role? CNS Drugs. 2003;17(6):373-81.
Simons DG, Mense S. Understanding and measurement of muscle tone as related to clinical muscle pain. Pain. Mar. 1998;75(1):1-17.
Boukhris A, Feki I, Denis E, Miladi MI, Brice A, Mhiri C, Stevanin G. Spastic paraplegia 15: linkage and clinical description of three Tunisian families. Mov Disord. Feb. 15, 2008;23(3):429-33.
Brugman F, Scheffer H, Wokke JH, Nillesen WM, de Visser M, Aronica E, Veldink JH, van den Berg LH. Paraplegin mutations in sporadic adult-onset upper motor neuron syndromes. Neurology. Nov. 4, 2008;71(19):1500-5.
Roşulescu E, Stănoiu C, Buteică E, Stănoiu B, Burada F, Zăvăleanu M. Hereditary spastic paraplegia. Rom J Morphol Embryol. 2009;50(2):299-303.
Contino G, Novelli G. Hereditary spastic paraplegia: clinical genomics and pharmacogenetic perspectives. Expert Opin Pharmacother. Oct. 2006;7(14):1849-56.
Gormley ME Jr, Krach LE, Piccini L. Spasticity management in the child with spastic quadriplegia. Eur J Neurol. Nov. 2001;8 Suppl 5:127-35.
Wasner G, Deuschl G. Pains in Parkinson disease-many syndromes under one umbrella. Nat Rev Neurol. Apr. 17, 2012. doi: 10.1038/nrneurol.2012.54. [Epub ahead of print].
Ha AD, Jankovic J. Pain in Parkinson's disease. Mov Disord. Apr. 2012;27(4):485-91.
Chung EJ, Kim SJ. Tonic spasms in acute transverse myelitis. J Clin Neurosci. Jan. 2009;16(1):165-6.
Smith PF, Darlington CL. Recent developments in drug therapy for multiple sclerosis. Mult Scler. Apr. 1999;5(2):110-20.
What Are Muscle Relaxants and When Are They Used to Treat Pain? (http://abcnews.go.com/Health/TreatingPain/story?id=4047617), Christo,P., download May 30, 2012.
Multiple Sclerosis, Muscle Tone and Spasiticty (http://www.medhelp.org/tags/health_page/7687/Multiple-Sclerosis/Muscle-Tone-And-Spasticity?hp_id=159), downloaded May 30, 2012.
WebMD, Pain management: Spasticity (http://www.webmd.com/pain-management/pain-management-spasticity), download May 30, 2012.
Jacques Devulder, Flupirtine in Pain Management, Pharmacological Properties and Clinical Use, CNS Drugs, 2010; 24 (10) Adis Data Information BV (http://medi.ru/doc/140346.htm).
Spastic Paraplegia Foundation, Inc., Pain Management and Treatment (http://www.sp-foundation.org/content/community/pain-treatment.html), Redden,R., Feb. 26, 2011, 5 pages.
Cerebral Palsy Source, Quadriplegia and Cerebral Palsy (http://cerebralpalsysource.com/Types_of_CP/Quadriplegia_cp/index.html), copyright 2005, downloaded May 30, 2012.
Kuo et al., Inhibition of Na+ Current by Diphenhydramine and Other Diphenyl Compounds . . . , Molecular Pharmacology, 2000, 57(1):135-143.
Beck et al., Kreuzschmerzen in der Gynaekologischen Praxis, Gynaekologe, Springer Verlag, Berlin Germany, 2002, 35(5):490-494.

* cited by examiner

COMBINATIONS OF FLUPIRTINE AND SODIUM CHANNEL INHIBITING SUBSTANCES FOR TREATING PAINS

This application is a continuation of U.S. application Ser. No. 10/727,658, filed Dec. 5, 2003, which claims priority under 35 U.S.C. §119 to German application no. DE 10349729.3, filed Oct. 23, 2003, each of which the entire contents are incorporated herein by reference.

The invention relates to pharmaceutical combinations of potassium channel openers and sodium channel inhibitors for treating pains which are accompanied by an increase in muscle tone.

A number of different painful diseases are accompanied by an increase in skeletal muscle tone. In some cases, the pain generation is elicited by joint inflammations, and a painful body posture, which is frequently accompanied by painful muscle spasms, develops as a consequence. The treatment of these diseases includes benzodiazepines, for example; however, these compounds possess a marked potential for addiction and this limits their use. Frequently, treating the basic disease, e.g. the rheumatoid inflammation, does not result in corresponding, satisfactory therapeutic successes. For this reason, the additional administration of analgesics and/or skeletal muscle relaxants is often indicated.

In clinical practice, centrally acting muscle relaxants are used for alleviating abnormally elevated muscle tone in patients who are suffering from painful muscle spasms and/or rigidity in association with rheumatoid diseases or spasms in connection with neurological diseases. While a number of appropriate active compounds are available on the market, their clinical efficacy is frequently questionable or else limited by undesirable side effects.

The Na+ channel-inhibiting substances constitute one class of these active compounds. Evidence exists that these substances are able to relieve an increase in muscle tone. It has been shown that, in clinically relevant concentration, propofol has a marked inhibitory effect on the sarcolemma sodium channels. This mechanism could contribute to reducing muscle tone (Haeseler et al., Anesth Analg 2001; 92:1192-8). It has also been shown that inhibiting the Na+ channels inhibits neurotransmitter release from the presynaptic termini (Obrenovitch, Int Rev Neurobiol 1997; 40:109-35). The neuroprotective active compound riluzole is a sodium channel inhibitor and an antiexcitotoxic substance which is used for treating amyotrophic lateral sclerosis. Kennel. et al. (J Neurol Sci 2000; 180:55-61) have recently shown that riluzole significantly delays the onset of the paralysis, and retards the progress of the functional parameters connected to muscle strength, in a mouse model of motoneuron disease. In a mouse model of heritable myotonia (De Luca et al., J Pharmacol Exp Ther 1997; 282:93-100), metilexin, an antiarrhythmic and antimyotonic substance, blocks the skeletal muscle sodium channels (Duranti et al., Eur J Med Chem 2000; 35:147-56) and relieves the hyperexcitability of the skeletal muscles. That the function of the skeletal muscle sodium channels is important in maintaining normal tone is supported by the fact that it has been possible to connect mutations in the gene for the a-25 subunit. of the voltage-induced Na+ channel (SCN4A) with inherited, nondystrophic myotonia. Interestingly, the myotonia resolved dramatically on administration of the Na+ channel-inhibiting substance flecainide (Rosenfeld et al., Ann Neurol 1997; 42:811-4).

Tolperisone is a centrally acting muscle relaxant which is relatively well tolerated clinically. To date, relatively few publications have dealt with the mechanism of action of tolperisone-like compounds. Tolperisone suppresses transmission of the spinal segment reflex and effectively reduces C fiber-induced transmission in the afferent nerves both in vivo and in vitro (Farkas et al., Neurobiology 1997; 5:57-58). As compared with lidocaine, a local anesthetic, the substance has less of a blocking effect on transmission in the A fibers. It characteristic effect is that of strongly inhibiting the monosynaptic and polysynaptic spinal reflexes (Farkas et al. Neurobiology 1997; 5:57-58, Kocsis et al., Acta Pharm Hung 2002; 72(1):49.-61, Okada et al., Jpn. J Pharmacol 2001; 86:134-136). In rats, Ono et al. (J Pharmacobio Dynam 1984; 7:171-178) showed that tolperisone exhibits an effect like that of a local anesthetic ("membrane-stabilizing") both in motor neurons and in primary afferents in vivo as well as on the peripheral nerves in vitro. The effect of tolperisone appears to be similar to that of lidocaine, which is known to act as an inhibitor of voltage-dependent sodium channels (Strathmann 2002, www.ifap-index.de/bda/hausarzt/19-2002/6483.pdf). It has been shown that tolperisone, like lidocaine, blocks the tetrodotoxin (TTX)-sensitive and TTX-resistant currents and in this way gives rise to an inhibitory effect on both types of voltage-dependent sodium. channels (Bastigkeit, MMW-Forschr Med 2000; 142:50-51, Farkas et al., 2000, http://www.asso.univparis5.fr/ewcbr/Francais/EWCBR2000/Abstracts/ABST126.htm; Kocsis et al., Acta Pharm Hung 2002; 72(1):49-61). It is probable that the mechanism of action of tolperisone in this connection differs somewhat from that of lidocaine. In addition, evidence exists that tolperisone lowers sodium permeability. This effect could be responsible for the excitability-reducing effect of tolperisone and consequently for the antispastic effect which has been recorded in clinical observations (Hinck and Koppenhofer, Gen Physiol Biophys 2001; 20:413-29). In addition, voltage-clamp experiments performed on snail neurons showed that tolperisone and its analogs inhibit voltage-dependent calcium flows (Novalies-Li et al., Eur J Pharmacol 1989; 168:299-305). Tolperisone analogs such as eperisone and silperisone exhibited similar behavior in electrophysiological experiments. Thus, it has been shown, for example, that silperisone reduces sodium permeability (During and Koppenhofer, Gen Physiol Biophys 2001; 20:157-73). It can be concluded from this that these substances might be able to reduce spastic skeletal muscle tone.

It has furthermore been shown, in clinical studies, that these substances are able to alleviate painful spasms which are associated with neurological or rheumatoid diseases. The effective employment of tolperisone in treating muscle spasms has been reported (Pratzel et al., Pain 1996; 67:417-25). Some derivatives of tolperisone, e.g. eperisone, also exhibited efficacy in the treatment of painful muscle spasms (Bose, Methods Find Exp Clin Pharmacol 1999; 21:209-13). Under certain pathological conditions, neurons are in a state of continuous depolarization, resulting in their sodium channels reacting more sensitively to the inhibitory effects of particular substances. This provides the possibility of alleviating muscle spasms and pain while preserving a favorable side-effect profile. More recent data indicate that tolperisone and its analogs exert selectively inhibitory effects on voltage-dependent sodium channels. This mechanism could be responsible for their spinal reflex-suppressing and muscle-relaxing effect. In addition, this property could produce the pain-alleviating effect which, because of the small differences which have been observed, could, in contrast to lidocaine, be free of side effects.

The potassium channel openers constitute another class of muscle-relaxing substances. The substances include flupirtine, for example, which belongs to a class of triaminopyridines and which is used as a nonopioid analgesic possessing muscle-relaxing properties. It has been shown that flupirtine reduces skeletal muscle tone when it is used in doses which are comparable to those of the antinociceptive effect (Nickel et al., Arzn Forsch/Drug Res 1990a; 40:909-11).

Since diazepam and other benzodiazepines are frequently used as muscle relaxants, it was obvious to compare the pharmacodynamic properties of flupirtine with those of the benzodiazepines. In receptor binding studies, no affinity for specific [3H] flunitrazepam was detected up to a concentration of 10 pmol/l (Nickel et al., Arzn Forsch/Drug Res 1990b; 40:905-908). Marked differences in the profiles induced by flupirtine and benzodiazepines, respectively, were demonstrated in regard to the changes in the EEG (Nickel, Postgrad Med J 1987; 63:19-28). Electrophysiological investigations showed that flupirtine influences GABAergic transmission by potentiating the GABA effect (Weiser et al., Arch Pharmacol 1992; 346(Suppl.):R22). Data from in vitro and in vivo analyses suggest that flupirtine behaves like a functional N-methyl-D-aspartate_ (NMDA) antagonist. It could be concluded from this that this mechanism could be involved in the muscle-relaxing effect of flupirtine (Schwarz et al., Neuroreport 1994; 5:1981-4). More recent investigations demonstrate that flupirtine activates voltage-independent. potassium channels (Kornhuber et al., J Neural Transm 1999; 106:857-67). This potassium channel-opening effect of flupirtine could be responsible for its analgesic and skeletal muscle-relaxing effect.

The prior art which has been described shows clearly that, while there are a number of substances which are used for treating pain conditions involving an increase in muscle tone, undesirable side effects frequently set limitations to their use. For example, at higher doses, flupirtine exhibits ne urotoxic effects such as drowsiness and coordination disturbance. While tolperisone does not exhibit any severe undesirable side effects, its activity and the duration of its effect in connection with muscle relaxation are not satisfactory, possibly due to its relatively low bioavailability and its short half-life in humans (Ito et al., Arch Int Pharmacodyn Ther 1985; 275: 105-22), Matsunaga et al., Jpn J Pharmacol 1997; 73:215-20).

The object of this invention is therefore that of providing a pharmaceutical for treating pains which are accompanied by an increase in muscle tone, which pharmaceutical exhibits less serious side effects while having a comparable efficacy or else exhibits a higher activity at the same dose.

According to the invention, it was possible to achieve this by means of the novel combination of a potassium channel opener and a sodium channel inhibitor.

It was possible to show that the combination of sodium channel-inhibiting or -influencing active compounds and potassium channel openers increases the muscle-relaxing effect.

The following may, for example, be employed as Na+ channel-inhibiting or -influencing substances: tolperisone and its analogs eperisone and silperisone, riluzole, propafenone, lidocaine, flecainide and metixen, as well as their pharmaceutically utilizable salts.

Potassium channel opener which may be cited, by way of example, are flupirtine.

Particular preference is given, in this connection, to the combination of tolperisone, or its analogs, and flupirtine, or their pharmaceutically utilizable salts. The combination according to the invention makes the treatment of pains which are accompanied by an increase in muscle tone more effective and more reliable. The combination of Na channel-inhibiting or -influencing substances and potassium channel openers such as flupirtine leads either to an increase in the therapeutic effect or an improvement in tolerability. For example, it has been shown that Na channel-inhibiting or -influencing active compounds such as tolperisone can amplify the muscle-relaxing effect of flupirtine, and vice versa. However, what is surprising, and unexpected for the skilled person, is, in particular, the effect thattolperisone superadditively amplifies the skeletal muscle-relaxing effect of flupirtine and vice versa. By contrast, tolperisone does not amplify the neurotoxicity of flupirtine.

The combination of the two substances can be used for treating pains in connection with diseases of the skeletal musculature which are accompanied by hypermyotonia and restricted mobility, in particular those which are elicited by injuries to the spinal cord, osteoporosis, arthritis and ankylosis/spastic conditions. It is also effective in connection with pains of the following origin: lumboischial pains, neurolathyrism, arthritis, diseases of the peripheral circulatory system, climacteric muscular and vascular complaints, trismus, myogenic headaches, rheumatic diseases which are accompanied by muscle hypertonia, spasms, pain, inflammatory symptoms and restricted mobility, and multiple sclerosis, and in the postoperative treatment of traumatic patients and for treating lower spastic paraparesis syndrome: lower paraspasm, transverse myelitis, multiple sclerosis, heritable inferior spastic paraplegia (Stuempel paraplegia), disturbances of the spinal blood circulation, cerebral paralysis involving lower spastic paresis, tetraparesis in connection with cervical myelopathy, vertebral dysplasia, tension headache and cervical brachialgia.

PHARMACOLOGICAL EXAMPLES

1: Muscle-Relaxing Effect on Reserpine-Induced Muscular Rigidity in Rats

Results

Both flupirtine and tolperisone reduce reserpine-induced skeletal muscle rigidity in conscious rats in a dose-dependent manner. The intraperitoneal (i.p.) $ED_{50}$ for flupirtine was 6.45 mg/kg. The $ED_{50}$ value for tolperisone was 32.4 mg/kg i.p.

The results given in tables 1 and 2 clearly show that the skeletal muscle-relaxing effect of flupirtine is surprisingly amplified superadditively by tolperisone, and vice versa.

TABLE 1

Effect of intraperitoneally administered flupirtine in combination with tolperisone on reserpine-induced skeletal muscle rigidity in conscious rats.

| Treatment | | Muscle relaxation (%) | |
|---|---|---|---|
| | | calculated | measured |
| Flupirtine 5 mg/kg | +Tolperisone 12.5 mg/kg | 52.2 | 71.1* |
| Flupirtine 5 mg/kg | +Tolperisone 25 mg/kg | 75.4 | 90.7* |
| Flupirtine 5 mg/kg | +Tolperisone 50 mg/kg | 121.0 | 163.2* |

TABLE 2

Effect of intraperitoneally administered tolperisone in combination with flupirtine on reserpine-induced skeletal muscle rigidity in conscious rats.

| Treatment | | Muscle relaxation (%) | |
|---|---|---|---|
| | | calculated | measured |
| Tolperisone 25 mg/kg | +Flupirtine 1 mg/kg | 44.7 | 60.2* |
| Tolperisone 25 mg/kg | +Flupirtine 3 mg/kg | 60.0 | 81.4* |
| Tolperisone 25 mg/kg | +Flupirtine 5 mg/kg | 75.4 | 92.1* |

Description of the Experiment

Male Sprague-Dawley rats weighing 200-220 g were kept in groups of two under standard conditions (temperature 22° C., humidity 40-60%) without any restriction in food or water. Illumination was provided from 6 a.m. to 6 p.m. The experiments were approved by the local animal health committee which was responsible for the protection and proper use of experimental animals.

The experimental approach has already been described in detail (Nickel et al. Arzn Forsch/Drug Res 1997; 47:1081-6). In brief, the rigidity of the skeletal muscle was measured by consecutively measuring the resistance of the flexor and extensor muscles which act in opposition when stretching and bending the foot in the joint. The pressure differences which were generated by the movement of the foot were recorded continuously. The signals were analyzed using a PC program which calculated the resistances of the flexor and extensor at the foot over periods of 10 min.

The active compounds were prepared freshly every day and were administered simultaneously i.p. at various doses 16 h after the reserpine injection (2 mg/kg, intraperitoneally).

The statistical analysis of the differences between the calculated and measured values was performed by means of a one-way. ANOVA. Asterisks (*) denote the significant level $p<0.01$.

2: Investigations of Skeletal Muscle Tone in Mice in the "Inclined Screen Test"

Results

The surprising results described in example 1 were verified convincingly in an experiment using mice.

Both flupirtine and tolperisone decrease skeletal muscle tone in conscious mice in a dose-dependent manner and, in so doing, provide information about their muscle-relaxing effect. The intraperitoneal (i.p.) $ED_{50}$ for flupirtine is 10.8 mg/kg. The $ED_{50}$ value for tolperisone is 51.0 mg/kg i.p.

The results given in tables 3 and 4 clearly show that, when various doses of flupirtine and tolperisone are administered simultaneously i.p., the skeletal muscle-relaxing effect of flupirtine is amplified superadditively by tolperisone, and vice versa.

TABLE 3

Effect of intraperitoneally administered flupirtine in combination with tolperisone on the skeletal muscle tone of conscious mice.

| Treatment | | Number of animals falling from the inclined surface in (%) | |
|---|---|---|---|
| | | calculated | measured |
| Flupirtine 1 mg/kg | +Tolperisone 12.5 mg/kg | 14 | 54* |
| Flupirtine 1 mg/kg | +Tolperisone 25 mg/kg | 28 | 62* |
| Flupirtine 1 mg/kg | +Tolperisone 50 mg/kg | 54 | 75* |

TABLE 4

Effect of intraperitoneally administered tolperisone in combination with flupirtine on the skeletal muscle tone of conscious mice.

| Treatment | | Number of animals falling from the inclined surface in (%) | |
|---|---|---|---|
| | | calculated | measured |
| Tolperisone 25 mg/kg | +Flupirtine 1 mg/kg | 28 | 50* |
| Tolperisone 25 mg/kg | +Flupirtine 3 mg/kg | 37 | 60* |
| Tolperisone 25 mg/kg | +Flupirtine 5 mg/kg | 46 | 70* |

Description of the Experiment

NMRI mice weighing 22-24 g were kept in groups of four under standard conditions (temperature 22° C., humidity 40-60%) without any restriction in food and water. Illumination was provided from 6 a.m. to 6 p.m. All the experiments were approved by the local animal health committee which was responsible for the protection and proper use of experimental animals.

What is termed the "30 degrees inclined screen test" (Simiand et al., Arch Int Pharmacodyn Ther 1989; 297:272-85) was used as a pharmacological model which enables predictions to be made regarding muscle-relaxing properties. The inclined screen consists of a wooden frame containing a wire gauze screen which can be inclined at any arbitrary angle (in this present case: 80°). The lower part of the screen is located 15 cm above the table. The animals are placed on the inclined screen and their ability to remain on the inclined screen is observed over a period of 30 s. The number of animals which fall from the screen is counted and the proportion it represents of the total number in each group is calculated. The active compounds were prepared freshly every day and were administered simultaneously i.p. at various doses, at 1 h before beginning the experiments, for analyzing the skeletal muscle tone.

The statistical analysis of the differences between the calculated and measured values were performed by means of a one-way ANOVA. Asterisks (*) denote the significant level $p<0.01$.

3: Possible Neurotoxic Effects of the Substances, as 25 Measured in a Rotating Rod Test Performed on Rats Results Centrally acting substances may have neurotoxic side effects which could restrict their therapeutic use. The results given in tables 5 and 6 clearly show that motor coordination is additively affected by the combination of flupirtine and tolperisone. It is not possible to observe any superadditive effect, i.e. the combination of flupirtine+tolperisone does not lead to undesirable central nervous effects being increased.

TABLE 5

Use of the rotating rod to determine the effect of intraperitoneally administered flupirtine in combination with tolperisone on motor coordination in rats.

| Treatment | | Number of animals remaining on the rotating rod in (%) | |
|---|---|---|---|
| | | calculated | measured |
| Flupirtine 1 mg/kg | +Tolperisone 12.5 mg/kg | 38 | 42 |
| Flupirtine 1 mg/kg | +Tolperisone 25. mg/kg | 50 | 49 |
| Flupirtine 1 mg/kg | +Tolperisone 50 mg/kg | 70 | 67 |

TABLE 6

Use of the rotating rod to determine the effect of intraperitoneally administered tolperisone in combination with flupirtine on motor coordination in rats.

| Treatment | | Number of animals remaining on the rotating rod in (%) | |
|---|---|---|---|
| | | calculated | measured |
| Tolperisone 25 mg/kg | +Flupirtine 1 mg/kg | 49 | 50 |
| Tolperisone 25 mg/kg | +Flupirtine 3 mg/kg | 57 | 50 |
| Tolperisone 25 mg/kg | +Flupirtine 5 mg/kg | 66 | 67 |

Description of the Experiment

Male Sprague-Dawley rats weighing 200-220 g were kept in groups of two under standard conditions (temperature 22° C., humidity 40-60%) without any restriction in food or water. Illumination was provided from 6 a.m. to 6 p.m. The experiments were approved by the local animal health committee which was responsible for the protection and proper use of experimental animals.

The motor coordination and balance of the animals were analyzed in what is termed the "rotating rod test" (Jones and Roberts, J. Pharm Pharmacol 1968; 20:302-304). The animals are placed on a rotating rod (diameter 10 cm; length 60 cm; 5 rpm) and, after a period of 2 minutes, the number of animals remaining on the rod is counted. The active compounds are prepared freshly every day and administered simultaneously intraperitoneally, at various doses, 30 min before beginning the experiments.

The described experiments clearly demonstrate the effects of the flupirtine/tolperisone combination. It can be deduced from the fact that potassium channel openers, on the one hand, and sodium channel-inhibiting or -influencing substances, on the other hand, have comparable mechanisms of action that other combinations of compounds from these substance classes will have the same positive effect.

The combinations of Na+ channel-inhibiting or -influencing active compounds and potassium channel openers, and of their pharmaceutically utilizable salts, can be administered in all oral, enteral, rectal, lingual, intravenous, intramuscular, intraperitoneal, transdermal, subcutaneous or intracutaneous administration forms. Examples of preferred oral administration forms are tablets, film-coated tablets, sugar-coated tablets, hard gelatin capsules, soft gelatin capsules, chewing tablets, sucking tablets, syrup, controlled release preparations (e.g. dual formulation, delayed-release formulation), pellets, chewing tablets or soluble granules. Examples of other suitable administration forms are: solutions for injection, suspensions, suppositories, creams, ointments, gels, transdermal administration forms and subcutaneous or intracutaneous implants.

The substances can be administered simultaneously, consecutively or in a fixed combination. They can be administered together in one administration form or in two administration forms which can be identical or different. They can be administered simultaneously or consecutively, either briefly one after the other or at longer time intervals, e.g. flupirtine in the evening and tolperisone in the morning.

The active compounds can be administered between 1 and 8 times daily, in an adequate quantity to achieve the desired affect. The active compounds are preferably administered from once to four times daily.

The daily dose should correspond to the approved quantities of the substances which are in each case employed in the combination. For the preferred combination, this is, for example, between 150 and 450 mg of tolperisone/day. in adults, with the quantity of flupirtine being 100-800 mg/day, preferably between 200 and 400 mg/day.

The invention claimed is:

1. A method of treating pain which is associated with abnormally elevated muscle tone associated with a disease or disorder, comprising administering to a patient experiencing pain which is associated with abnormally elevated muscle tone associated with a disease or disorder a combination of a therapeutically effective amount of flupirtine or a therapeutically utilizable salt thereof and a therapeutically effective amount of a sodium channel-inhibiting substance, wherein the sodium channel-inhibiting substance is of tolperisone, or a pharmaceutically utilizable salt thereof, wherein the therapeutically effective amounts are therapeutically superadditive.

2. The method of claim 1, wherein the pain is associated with a neuralgia.

3. The method of claim 1, wherein the pain is associated with arthritis or arthrosis.

4. The method of claim 1, wherein the pain is associated with chronic or episodic tension headache.

5. The method of claim 1, wherein the pain is associated with a lower spastic paraparesis syndrome.

6. The method of claim 1, wherein the pain is associated with spastic tetraparesis in connection with cervical myelopathy, cervical brachialgia or vertebral dysplasia.

7. The method of claim 1, wherein the pain is associated with Parkinson's disease.

8. A method of producing a medicament for treating pain which is associated with abnormally elevated muscle tone by the method of claim 1, comprising combining the therapeutically effective amount of flupirtine or a therapeutically utilizable salt thereof with the therapeutically effective amount of the sodium channel-inhibiting substance, wherein the sodium channel-inhibiting substance is tolperisone, wherein the medicament is for oral, rectal, intravenous, transdermal, subcutaneous or intracutaneous administration.

9. The method of claim 5, wherein the lower spastic paraparesis syndrome is selected from the group consisting of lower paraspasm, transverse myelitis, multiple sclerosis, heritable inferior spastic paraplegia, disturbances of the spinal blood circulation and cerebral paralysis involving lower spastic paresis.

* * * * *